United States Patent
Attia et al.

(10) Patent No.: US 11,337,677 B2
(45) Date of Patent: May 24, 2022

(54) VOLUME RENDERED ULTRASOUND IMAGING

(71) Applicant: KONINKLIJKE PHILIPS N.V., Eindhoven (NL)

(72) Inventors: Emmanuel Mocé Serge Attia, Paris (FR); Cristian Lorenz, Hamburg (DE); David Nigel Roundhill, Woodinville, WA (US); Alasdair Dow, Snohomish, WA (US); Benoit Jean-Dominique Bertrand Maurice Mory, Mercer Island, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 212 days.

(21) Appl. No.: 16/495,314

(22) PCT Filed: Mar. 19, 2018

(86) PCT No.: PCT/EP2018/056792
§ 371 (c)(1),
(2) Date: Sep. 18, 2019

(87) PCT Pub. No.: WO2018/172236
PCT Pub. Date: Sep. 27, 2018

(65) Prior Publication Data
US 2020/0015785 A1    Jan. 16, 2020

(30) Foreign Application Priority Data

Mar. 20, 2017  (EP) ..................................... 17305300

(51) Int. Cl.
*A61B 8/08*    (2006.01)
*A61B 8/00*    (2006.01)
(Continued)

(52) U.S. Cl.
CPC ............ *A61B 8/483* (2013.01); *A61B 8/0866* (2013.01); *A61B 8/466* (2013.01); *A61B 8/5223* (2013.01);
(Continued)

(58) Field of Classification Search
CPC ....... A61B 8/483; A61B 8/0866; A61B 8/466; A61B 8/5223; A61B 8/469; A61B 8/488;
(Continued)

(56) References Cited

U.S. PATENT DOCUMENTS 6,280,387 B1 *  8/2001  Deforge ................... A61B 8/06
                                                          128/916
6,334,847 B1   1/2002  Fenster et al.
(Continued)

FOREIGN PATENT DOCUMENTS

DE    10210466 A1   10/2003
EP    2302414 A2    3/2011
(Continued)

OTHER PUBLICATIONS

International Search and Written Opinion for International Application No. PCT/EP2018/056792, filed Mar. 19, 2018, 14 pages.
(Continued)

*Primary Examiner* — Bo Joseph Peng

(57) ABSTRACT

An ultrasound image processing apparatus (200) is disclosed for obtaining a biometric measurement of an anatomical feature of interest from a 3D ultrasound image. The apparatus comprises a display apparatus (50) communicatively coupled to a processor arrangement (210) adapted to render a volumetric ultrasound image (300) from the 3-D ultrasound image and control the display apparatus to display said rendered image; receive a plurality of user inputs (303) highlighting the anatomical feature of interest, each input corresponding to a pixel of the displayed volumetric ultra-
(Continued)

sound image; estimate a depth of each of said pixels in the volumetric ultrasound image (300); define a 3-D path (307) in the volumetric ultrasound image based on the received user inputs along said estimated depths; perform a processing operation based on the defined 3-D path; and control the display apparatus to display the processing operation result, wherein the processing operation based on the defined 3-D path comprises at least one of a measurement of a length of the 3-D path (307); a reorientation of the rendered volumetric ultrasound image (300); and a generation of a 2-D image slice (400) of the 3-D ultrasound image based on the defined 3-D path. Also disclosed are an ultrasound imaging system including such an ultrasound image processing apparatus, a computer-implemented method and a computer program product for implementing this method on a computer.

20 Claims, 8 Drawing Sheets

(51) Int. Cl.
  *G06T 7/50* (2017.01)
  *G06T 7/00* (2017.01)
  *G06T 7/60* (2017.01)
(52) U.S. Cl.
  CPC .............. *A61B 8/469* (2013.01); *A61B 8/488* (2013.01); *A61B 8/5246* (2013.01); *G06T 7/0012* (2013.01); *G06T 7/50* (2017.01); *G06T 7/60* (2013.01); *G06T 2207/10136* (2013.01)
(58) Field of Classification Search
  CPC ......... A61B 8/5246; A61B 8/523; G06T 7/50; G06T 7/0012; G06T 7/60; G06T 2207/10136; G06T 2219/008; G06T 19/00; G16H 50/30
  See application file for complete search history.

(56) References Cited

U.S. PATENT DOCUMENTS

| | | | |
|---|---|---|---|
| 8,891,881 B2 | 11/2014 | Gupta et al. | |
| 2010/0177177 A1* | 7/2010 | Sonnemans | G06T 7/0012 |
| | | | 348/61 |
| 2011/0304619 A1* | 12/2011 | Fu | G06K 9/00201 |
| | | | 345/420 |
| 2013/0127836 A1* | 5/2013 | Joshi | G06T 17/20 |
| | | | 345/419 |
| 2013/0182902 A1* | 7/2013 | Holz | G06T 7/75 |
| | | | 382/103 |
| 2017/0060253 A1 | 3/2017 | Kang et al. | |

FOREIGN PATENT DOCUMENTS

| | | |
|---|---|---|
| EP | 3106096 A1 | 12/2016 |
| JP | 2012081257 A | 4/2012 |
| JP | 2016079080 A | 5/2016 |
| JP | 2016083192 A | 5/2016 |

OTHER PUBLICATIONS

Hatanaka, et al., "Reference Intervals for Fetal Ear Length Between 19 and 24 Weeks of Pregnancy on 3-Dimensional Sonography", J. Ultrasound Med 2011; 30: pp. 1185-1190.

* cited by examiner

300

400

VOLUME RENDERED ULTRASOUND IMAGING

RELATED APPLICATIONS

This application is the U.S. National Phase application under 35 U.S.C. § 371 of International Application No. PCT/EP2018/056792, filed on Mar. 19, 2018, which claims the benefit of European Application No. 17305300.0, filed Mar. 20, 2017. These applications are hereby incorporated by reference herein.

FIELD OF THE INVENTION

The present invention relates to an ultrasound image processing apparatus for obtaining a biometric measurement from a 3D ultrasound image, comprising a display apparatus communicatively coupled to a processor arrangement adapted to render a volumetric ultrasound image from a 3-D ultrasound image and control the display apparatus to display said rendered image.

The present invention further relates to an ultrasound system including such an ultrasound image processing apparatus.

The present invention further relates to a computer-implemented method to render a volumetric ultrasound image from a 3-D ultrasound image and control a display apparatus to display said rendered image.

The present invention further relates to a computer program product for implementing such a method on an ultrasound imaging processing apparatus.

BACKGROUND OF THE INVENTION

Ultrasound plays an essential role in many diagnostic imaging techniques including but not limited to fetal imaging. Ultrasonic imaging is routinely used during pregnancy to assess the development of a fetus in the mother's womb, for example to detect structural anomalies in the fetus. The traditional way for a clinician to acquire an image of each required view of the fetus is to manipulate an ultrasound probe while in acoustic contact with the abdomen of the mother until a desired anatomical orientation is in the plane of the 2-D imaging probe. If multiple views are to be generated with such a procedure, there is a risk of missed abnormalities because obtaining and analyzing these views requires high skill (e.g. fetal echocardiography is very operator-dependent) whilst in addition the fetus may be moving during the procedure, requiring the clinician to reorient himself or herself with the fetus each time the fetus moves.

With the advent of three dimensional (3-D) ultrasound image acquisition, it is now possible to capture a large volume of the fetus and to perform computed rendering of 2-D views at any point in time, e.g. even after the patient (the fetus) is released. The 3-D acquisition procedure may be conducted by making a slow sweep of the 2-D image plane over the fetus (mechanical steering) or by electronically steering the ultrasound beams over the fetus. User-directed image processing may then be used for evaluation of the captured image volume, i.e. to evaluate the fetal anatomy. As such, 3-D ultrasound image acquisition is less operator-dependent and facilitates evaluation of the image volume along different views, for example to answer different diagnostic questions following the examination of the fetus.

Of particular interest to analyse the development of the fetus are so-called biometry measurements, which are used to check if the fetus is developing correctly, e.g. within expected tolerances. However, due to the complexity of the interpretation of 3-D ultrasound images, such as in volume rendering mode in which a 3-D volume of the fetus is imaged on a display device of the ultrasound imaging system, many clinicians prefer to perform such biometric measurements on 2-D ultrasound images, as they have greater confidence in the reliability of such measurements when obtained from 2-D images because it is more straightforward to obtain a visualization of the anatomical feature of interest in a desired plane, e.g. a plane along such a feature, despite the evidence provided by Alan Roberto Hatanaka et al., in "Reference Intervals for Fetal Ear Length Between 19 and 24 Weeks of Pregnancy on 3-Dimensional Sonography, J. Ultrasound Med. 2011; 30: 1185-1190 in which they demonstrate that 3-D ultrasound in volume rendering mode can produce biometric measurement accuracy comparable with 2-D ultrasound imaging with good inter-operator reproducibility. For example, a clinician may be concerned that an incorrect biometric measurement is obtained through effects such as foreshortening of an anatomical feature of interest, e.g. a fetal bone or the like due to the measurement being performed in a volumetric view in which the clinician is unaware of the fact that an anatomical feature of interest is visualized under an angle, causing an underestimation of its dimensions obtained through measurement by the clinician.

Consequently, 3-D (and 4-D) ultrasound imaging at present is largely used to provide the expecting parents with realistic images of their developing child, i.e. the fetus. This hampers the penetration of such 3-D and 4-D ultrasound imaging systems into medical facilities, given the investment required for such systems may be considered unjustifiable if the system is not routinely being used for diagnostic purposes. Hence, there exists a need to facilitate the evaluation of volume rendered 3-D images by a clinician.

EP 3 106 096 A1 discloses an ultrasound diagnosis apparatus including a display configured to display a first ultrasound image showing an object, a user input device configured to receive a user input for selecting first and second depths in the first ultrasound image and setting different three-dimensional (3D) rendering properties with respect to the first and second depths; and a controller configured to generate a second ultrasound image showing a 3D volume of the object based on the set 3D rendering properties, wherein the display is further configured to display the generated second ultrasound image. In particular, opacity values, a color, a shape of an ROI or a degree of focus may be set by the user according to a depth.

SUMMARY OF THE INVENTION

The present invention seeks to provide an ultrasound image processing apparatus facilitating accurate biometric measurements from a volume rendered ultrasound image.

The present invention further seeks to provide an ultrasound system including such an ultrasound image processing apparatus.

The present invention further seeks to provide a computer-implemented method facilitating accurate biometric measurements from a volume rendered ultrasound image.

The present invention further seeks to provide a computer program product for implementing such a method on an ultrasound imaging processing apparatus.

According to an aspect, there is provided an ultrasound image processing apparatus for obtaining a biometric measurement of an anatomical feature of interest from a 3-D ultrasound image, comprising a display apparatus communicatively coupled to a processor arrangement adapted to render a volumetric ultrasound image from the 3-D ultrasound image and control the display apparatus to display said rendered image; receive a plurality of user inputs highlighting the anatomical feature of interest, each input corresponding to a pixel of the displayed volumetric ultrasound image; estimate a depth of each of said pixels in the volumetric ultrasound image; define a 3-D path in the volumetric ultrasound image based on the received user inputs along said estimated depths; perform a processing operation based on the defined 3-D path; and control the display apparatus to display the processing operation result, wherein the processing operation based on the defined 3-D path comprises at least one of a measurement of a length of the 3-D path; a reorientation of the rendered volumetric ultrasound image; and a generation of a 2-D image slice of the 3-D ultrasound image based on the defined 3-D path.

Hence, an ultrasound image processing apparatus is provided in which a user can specify a number of points, e.g. two or more points on the display apparatus, for example by touching the screen of the display apparatus in case of a touchscreen display apparatus or by using any suitable user interface such as a mouse, trackball, or the like to highlight an anatomical feature of interest within the volumetric ultrasound image, which user-specified points are interpreted by the ultrasound image processing apparatus in the context of the rendered volumetric ultrasound image to identify a 3-D path in the image, based on which the processor arrangement may perform one or more of a number of operations based on the determined 3-D path. For example, the processor arrangement may determine the length of the 3-D path, which for example may be useful where the user has specified two (or more) points to obtain a measurement of an anatomical feature of interest identified by these points, where the 3-D path is typically mapped onto the anatomical feature of interest, thereby providing an accurate measurement of the dimension, e.g. length, of this anatomical feature. Alternatively, the 3-D path may be used to reorient the rendered volumetric ultrasound image such that the 3-D path is aligned with the viewing angle or perpendicular to the viewing angle along the rendered volumetric ultrasound image, thereby providing the user with an option to reorient the volumetric ultrasound image inner intuitive manner, e.g. to obtain a view of an anatomical feature of interest identified of the user-specified points on which the 3-D path is based. A particularly preferred processing option is that a (reformatted) 2-D image slice is extracted from the volumetric ultrasound image and displayed on the display apparatus to facilitate interpretation of the anatomical feature of interest by the user. Preferably, the 2-D image slice is generated such that the anatomical feature of interest, or at least a substantial part thereof, lies in the plane of the image slice, thereby reducing the risk of incorrect biometric measurement of the anatomical feature of interest by the user in case the user wishes to manually perform such a measurement.

The various embodiments of the present invention have in common that they are based on the insight that a volumetric ultrasound image typically includes depth information, e.g. in the form of a certain intensity iso-surface as obtained through texture rendering or depth information obtained using the viewing angle of the user in conjunction with the user-specified point based on which a view ray through the volumetric ultrasound image may be estimated, which view ray may be used to obtain image information along this view in order to find the depth in the volumetric ultrasound image having the highest contribution to the pixel intensity of the display apparatus pixel coinciding with the user-defined point. In this manner, the 3-D path may be accurately created along a surface contour of the anatomical structure of interest captured within the volumetric ultrasound image, which 3-D path may be utilized in further processing operations performed on the volumetric ultrasound image as explained above.

In an embodiment, the processor is adapted to generate the 3-D ultrasound image from a sequence of 2-D ultrasound images, which sequence for example may be captured through mechanical or electronic beam steering, or through manual migration of an ultrasound probe along a trajectory such as a body contour of a patient.

In an embodiment, the processor arrangement is adapted to generate a 2-D image slice based on the defined 3-D path by fitting a plurality of tangential planes to different regions of the defined 3-D path; selecting the tangential plane having the best fit with the defined 3-D path; and generating the 2-D image slice in accordance with the selected tangential plane. In this manner, the 2-D image slice of the volumetric ultrasound image can be accurately aligned with the 3-D path.

Optionally, the selected tangential plane is further based on a current view orientation of the rendered volumetric ultrasound image. For example, the best fitting plane within a defined range of view orientations around the current view orientation may be selected in order to avoid a sudden large change in the view orientation of the rendered volumetric ultrasound image, which may be confusing to the user of the ultrasound image processing apparatus.

In a further embodiment, the processor arrangement further is adapted to perform the biometric measurement on an anatomical feature of interest visible within the generated 2-D image slice; and control the display apparatus to display a result of the performed biometric measurement in order to provide a fully automated procedure to obtain such a biometric measurement. The processor arrangement may be adapted to control the display apparatus to display a result of the performed biometric measurement by controlling the display apparatus to display the generated 2-D image slice together with said result.

In order to obtain the biometric measurement, the processor arrangement may be adapted to perform the biometric measurement on an anatomical feature of interest visible within the generated 2-D image slice by defining a volume of interest associated with the defined 3-D path; and identifying the anatomical feature of interest within the volume of interest. This is a robust manner to identify the anatomical feature of interest associated with the user-specified points.

In such an automated biometric measurement, the anatomical feature of interest may be a priori known, for example because the user has specified which anatomical feature of interest the user is looking for, in which case of the anatomical feature of interest may be identified in the defined volume of interest in a straightforward manner, e.g. using an image filter and/or segmentation algorithm in order to identify the known anatomical feature of interest within the volume of interest. However, in a scenario in which it is not known which anatomical feature of interest the user is looking for, the processor arrangement may be adapted to identify the anatomical feature of interest within the volume of interest by applying a plurality of image filters to the volume of interest; and identifying the anatomical feature of interest based on the filter results obtained by said applying. In this manner, the anatomical feature of interest may be identified in an automated manner by using those filter results that result in the recognition of an anatomical feature with the highest degree of confidence, for example.

According to another aspect, there is provided an ultrasound imaging system comprising the ultrasound image processing apparatus of any of the herein described embodiments and an ultrasound probe for providing the ultrasound image processing apparatus with the 3-D ultrasound image data. Such an ultrasound probe typically is an ultrasound probe for capturing 3-D ultrasound images, i.e. by capturing the sequence of 2-D ultrasound images from which the 3-D ultrasound image can be rendered through mechanical or electronic steering.

According to yet another aspect, there is provided a computer-implemented method for obtaining a biometric measurement of an anatomical feature of interest from a 3-D ultrasound image, the method comprising receiving the 3-D ultrasound image; rendering a volumetric ultrasound image from the 3-D ultrasound image and controlling a display apparatus to display said rendered image; receiving a plurality of user inputs highlighting the anatomical feature of interest, each input corresponding to a pixel of the displayed volumetric ultrasound image; estimating a depth of each of said pixels in the volumetric ultrasound image; defining a 3-D path in the volumetric ultrasound image based on the received user inputs along said estimated depths; performing a processing operation based on the defined 3-D path; and controlling the display apparatus to display the processing operation result, wherein the processing operation based on the defined 3-D path comprises at least one of a measurement of a length of the 3-D path; a reorientation of the rendered volumetric ultrasound image; and a generation of a 2-D image slice of the 3-D ultrasound image based on the defined 3-D path. As explained above in the context of the ultrasound image processing apparatus, such a computer-implemented method facilitate interpretation of the volumetric ultrasound image by a user such as a clinician or sonographer by allowing the user to obtain a biometric measurement, reorient the rendered volumetric image or select a 2-D image slice in which an anatomical feature of interest lies in the plane of the slice in an intuitive and straightforward manner, e.g. by specifying the points through a user interface such as a touchscreen, mouse, trackball or the like. As explained above, in this manner a 3-D path may be constructed that accurately follows a feature such as a contoured surface within the volumetric ultrasound image.

The method may further comprise generating the 3-D ultrasound image from a sequence of 2-D ultrasound images, as explained above.

Generating a 2-D image slice based on the defined 3-D path may comprise fitting a plurality of tangential planes to different regions of the defined 3-D path; selecting the tangential plane having the best fit with the defined 3-D path; and generating the 2-D image slice in accordance with the selected tangential plane in order to obtain a good match between the defined 3-D path and the 2-D image slice to be displayed on the display apparatus as explained above. Such generating optionally comprises selecting the best fitting plane within a defined range of view orientations around the current view orientation of the rendered volumetric image in order to avoid a sudden large change in the view orientation of the rendered volumetric ultrasound image, which may be confusing to the user of the ultrasound image processing apparatus.

In an embodiment, the computer-implemented method further comprises performing the biometric measurement on an anatomical feature of interest visible within the generated 2-D image slice; and controlling the display apparatus to display a result of the performed biometric measurement, optionally wherein controlling the display apparatus to display a result of the performed biometric measurement comprises controlling the display apparatus to display the generated 2-D image slice together with said result, thereby providing a fully automated method of obtaining accurate biometric measurements from a rendered volumetric ultrasound image.

Performing the biometric measurement on an anatomical feature of interest visible within the generated 2-D image slice may comprise defining a volume of interest associated with the defined 3-D path; and identifying the anatomical feature of interest within the volume of interest in order to reliably identify the anatomical feature of interest as explained above.

Identifying the anatomical feature of interest within the volume of interest may comprise applying a plurality of image filters to the volume of interest; and identifying the anatomical feature of interest based on the filter results obtained by said applying in order to recognize an unknown anatomical feature of interest as explained above.

According to yet another aspect, there is provided a computer program product comprising a computer readable storage medium having computer readable program instructions embodied therewith for, when executed on a processor arrangement of an ultrasound image processing apparatus of any of the herein described embodiments, cause the processor arrangement to implement the method of any of the herein described embodiments.

BRIEF DESCRIPTION OF THE DRAWINGS

Embodiments of the invention are described in more detail and by way of non-limiting examples with reference to the accompanying drawings, wherein.

DETAILED DESCRIPTION OF THE EMBODIMENTS

Figure 1:
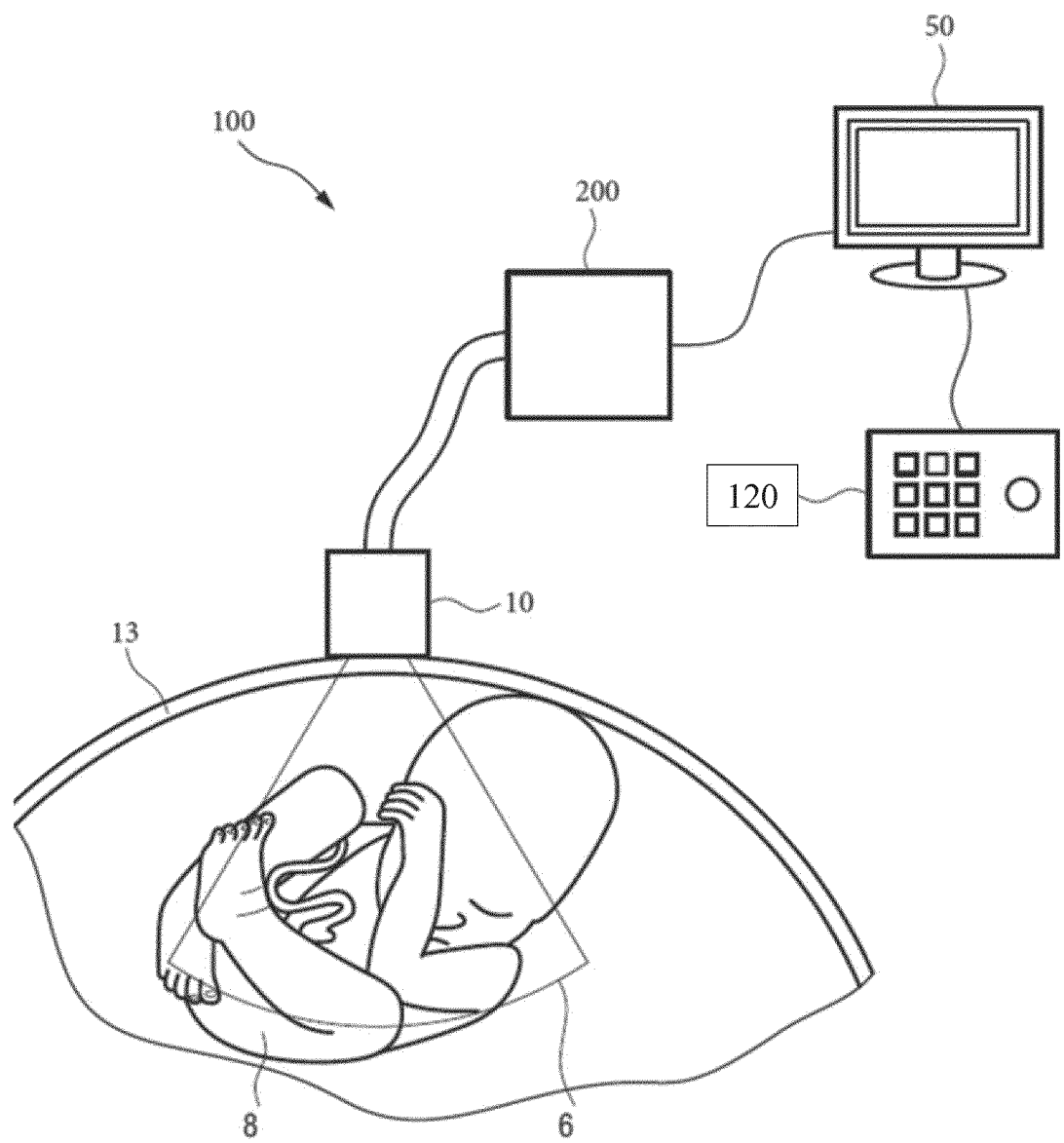
FIG. 1 schematically depicts an ultrasound imaging system according to an example embodiment in operation.

It should be understood that the Figures are merely schematic and are not drawn to scale. It should also be understood that the same reference numerals are used throughout the Figures to indicate the same or similar parts.

FIG. 1 shows a schematic illustration of an ultrasound imaging system 100 according to an example embodiment. The ultrasound imaging system 100 is applied to inspect a volumetric region of an anatomical site, in particular an anatomical site of a patient 13 including a fetus 8. The 3-D image of such a volumetric region will also be referred to as the imaging volume, whilst a 2-D slice of such a 3-D image will also be referred to as a volume slice.

The ultrasound imaging system 100 comprises an ultrasound probe 10 having at least one transducer array having a multitude of transducer elements for transmitting and/or receiving ultrasound waves. The transducer elements are preferably arranged in a two-dimensional (2D) array, which is constructed to electronically steer ultrasound beams within the volumetric region such that a three-dimensional ultrasound image frame of said region is provided. Alternatively, the array may be a one-dimensional array (1D) constructed to be mechanically steered through the volumetric region in order to provide a three-dimensional ultrasound image frame. The probe 10 is adapted to transmit ultrasound waves in a particular direction and to receive ultrasound waves from a particular direction which forms a field of view 6 for a given 3D image frame of the ultrasound probe 10. Such 3-D imaging is well-known per se and will therefore not be explained in further detail for the sake of brevity only.

In the embodiment shown in FIG. 1, the patient 13 is a pregnant person, wherein an anatomical entity to be inspected is a fetus 8, at least part of which is disposed in the field of view 6.

The ultrasound imaging system 100 further comprises an ultrasound image processing apparatus 200 such as a control unit, which typically comprises a processor arrangement 210 including one or more processing elements, and controls the provision of an ultrasound image via the ultrasound system 100. As will be explained further below, the ultrasound image processing apparatus 200 may receive ultrasound image data from the transducer array of the ultrasound probe 10 and provides a compounded three-dimensional (3D) ultrasound image, i.e. a volume rendered image, derived from the different ultrasound data sets of the fetus 8 in a volume rendering mode of the ultrasound system 100.

The ultrasound imaging system 100 further comprise a display device 50 for displaying the ultrasound image received from the ultrasound image processing apparatus 200. Still further, a user interface 120 is provided that may comprise any combination of keys or a keyboard and inputting devices and may be connected to the display device 50 and/or directly to the ultrasound image processing apparatus 200. Such inputting devices for example may include a mouse, trackball, or the like. Other suitable inputting devices will be immediately apparent to the skilled person. In the context of the present application, a user may convey a translation instruction to the ultrasound image processing apparatus 200 by moving an input device such as a trackball or mouse, by clicking a key, and so on. It should be understood that a translation instruction in some embodiments equates to the movement of an input device such as a trackball or mouse by the user. A particular example for a three-dimensional ultrasound system 100 may be the CX40 Compact Xtreme ultrasound system sold by the applicant. In general, matrix transducer systems as found on Philips iE33 systems or mechanical 3D/4D transducer technology as found, for example, on the Philips iU22 and HD15 systems may be applied in conjunction with the current invention.

Figure 2:
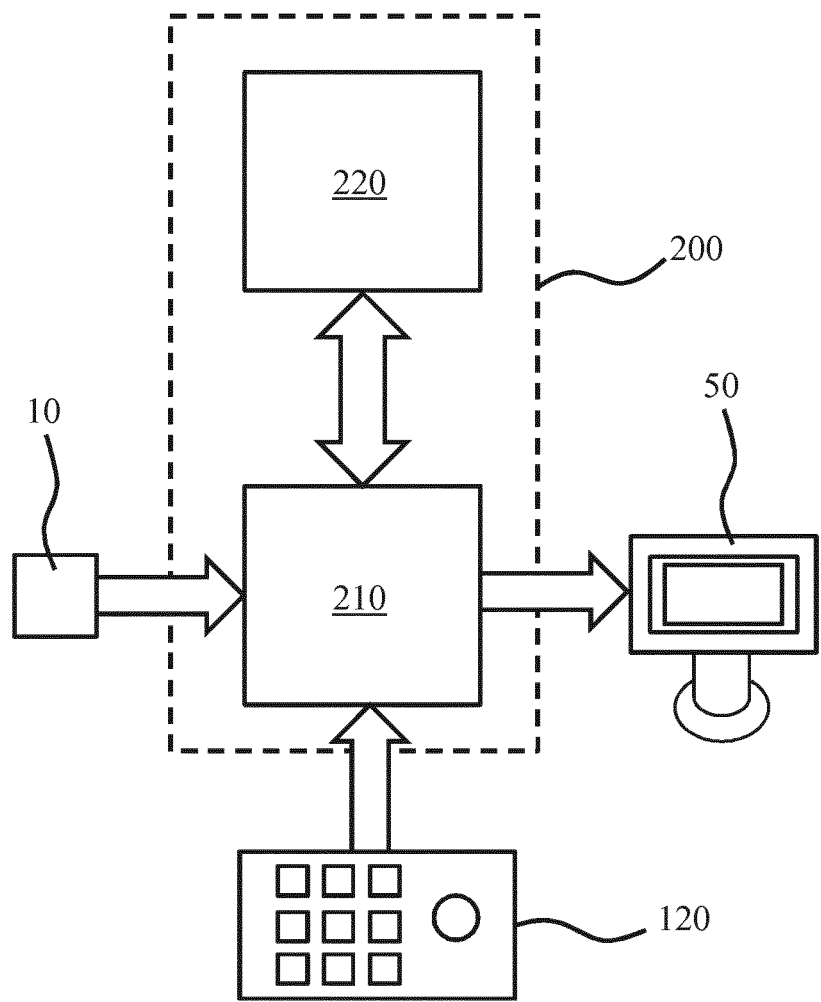
FIG. 2 schematically depicts an aspect of the ultrasound imaging system of FIG. 1 in more detail.

An example embodiment of the ultrasound image processing apparatus 200 is provided in more detail in FIG. 2, in which the ultrasound image processing apparatus 200 comprises at least a processor arrangement 210 and a data storage arrangement 220. The display device 50 may be separate to the ultrasound image processing apparatus 200 or may form part of the ultrasound image processing apparatus 200. Similarly, at least part of the user interface 120 may be separate to the ultrasound image processing apparatus 200 or may form part of the ultrasound image processing apparatus 200.

Figure 6:
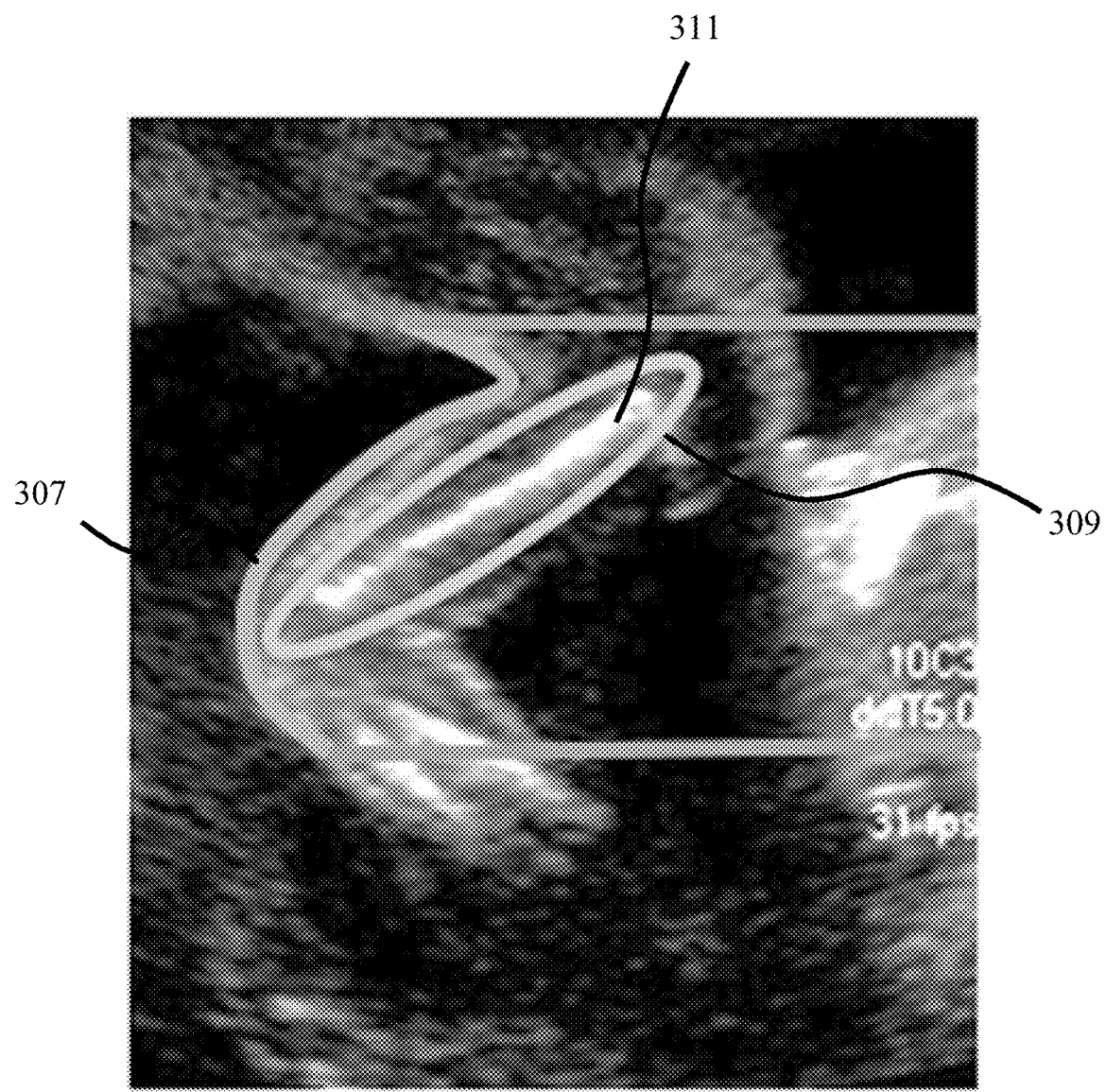
FIG. 6 schematically depicts the processing of the rendered volumetric ultrasound image based on the user-identified points of interest in accordance with an example embodiment of the present invention.

The processor arrangement 210 may include an ultrasound image processor adapted to process digital echo signals by spatial compounding in an ultrasound image processor, such as the ultrasound image processor 30 in the example embodiment of the ultrasound imaging system as schematically depicted in FIG. 6, which will be described in more detail below. The data storage arrangement 220 may comprise one or more memory devices, which may be discrete memory devices or may form part of the processor arrangement 210. For example, the data storage arrangement 220 may include a compound image memory unit, which may form part of the ultrasound image processor or may be separate to the ultrasound image processor. The compound image memory may be implemented as a 3D frame storage buffer and may be implemented as a dual port memory which can be written to and read from simultaneously. The use of such a R/W memory enables newly acquired 3D ultrasound image frames by the transducer array of the ultrasound probe 10 and the beamformer (to be described in more detail below) to be written into one area of the R/W memory while the data of other 3D image frames previously stored in the memory is read out and analyzed. The writing of new slice image data into the memory may be controlled by a write address controller while the reading of slice image data from other locations in the memory may be under the control of a read address controller, thereby facilitating real time image analyses and compounding. Of course, such a compound image memory unit equally may be used for evaluation of the imaging volume upon completion of its acquisition, e.g. after investigation of the patient.

Figure 3:
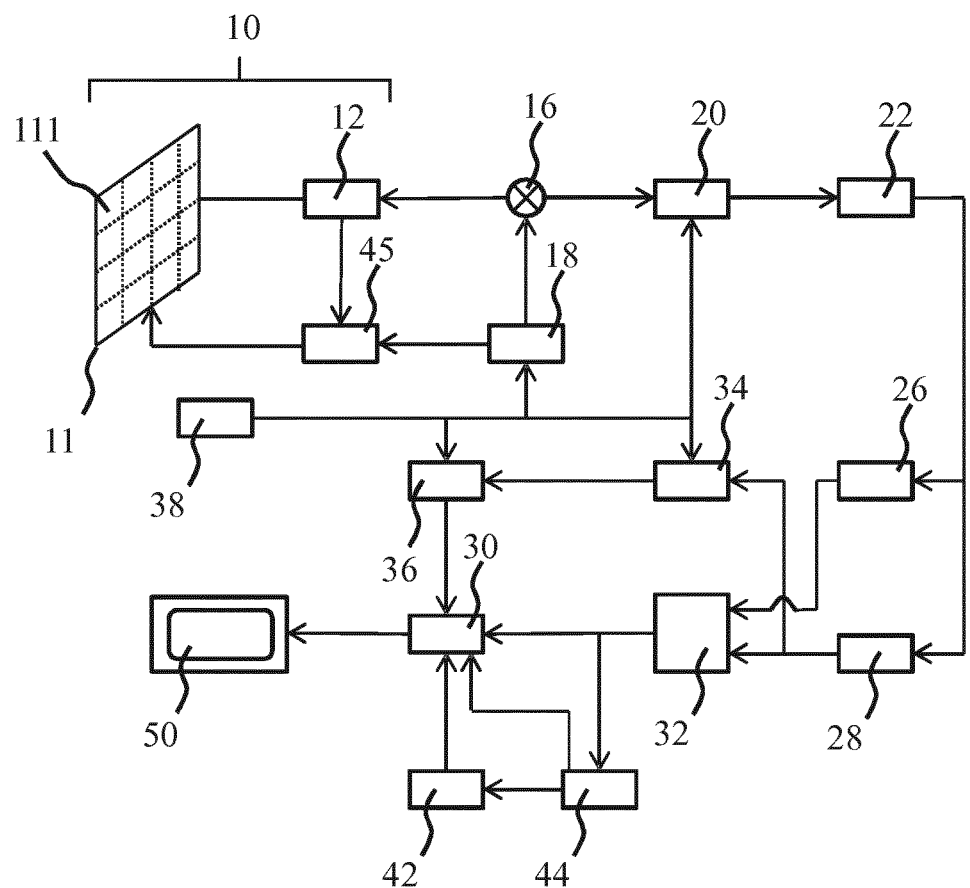
FIG. 3 schematically depicts a block diagram of an example embodiment of an ultrasound imaging system of the present invention.

FIG. 3 schematically depicts an example embodiment of an ultrasound imaging system 1 in which the ultrasound image processing apparatus 200 is provided as a user console to which the ultrasound probe 10 comprising an ultrasound transducer array 11 is communicatively coupled, e.g. using an appropriate cable or the like. It should however be understood that at least parts of the ultrasound imaging system 1 may be distributed, e.g. provided as a remote service, in particular those elements for which the skilled person will understand that these elements are deployed for the processing of the sonographic data captured with the ultrasound transducer array 10.

In particular, FIG. 3 schematically depicts a block diagram of an example embodiment of the electronics that may be deployed to interface with and control the ultrasound transducer array 11 for the generation of ultrasound waves, e.g. ultrasound pulses, and reception of ultrasound echoes, e.g. pulse echoes, e.g. for diagnostic imaging purposes. At least part of these electronics may be embodied by the processor arrangement 210. Therefore, it should be understood that although these electronics are identified by different reference numerals, this does not necessarily mean that these electronics are distinct to the processor arrangement 210.

The ultrasound transducer array 11 may be coupled to a microbeam former 12, which may be located in the ultrasound probe 10 in some embodiments, which controls transmission and reception of signals by the ultrasound transducer cells 111 of the ultrasound transducer array 11. Microbeam formers are capable of at least partial beam forming of the signals received by groups or "patches" of transducer element tiles for instance as described in U.S. Pat. No. 5,997,479 (Savord et al.), U.S. Pat. No. 6,013,032 (Savord), and U.S. Pat. No. 6,623,432 (Powers et al.) The microbeam former 12 may be coupled by a probe cable, e.g. coaxial wire, to a terminal, e.g. an ultrasound image processing apparatus 200 such as a user console device or the like, which apparatus may comprise a transmit/receive (T/R) switch 16 which switches between transmission and reception modes and protects the main beam former 20 from high energy transmit signals when a microbeam former is not present or used and the transducer array is operated directly by the main system beam former 20.

The transmission of ultrasonic beams from the ultrasound transducer array 11 under control of the microbeam former 12 may be directed by a transducer controller 18 coupled to the microbeam former by the T/R switch 16 and the main system beam former 20, which receives input from the user's operation of the user interface 120 through control panel 38. One of the functions controlled by the transducer controller 18 is the direction in which beams are steered and focused. Beams may be steered straight ahead from (orthogonal to) the transducer array, or at different angles for a wider field of view. The transducer controller 18 may be coupled to control a voltage source 45 for the ultrasound transducer array 110. For instance, the voltage source 45 may set the DC and AC bias voltage(s) that are applied to CMUT (capacitive micro-machined ultrasound transducer) elements 111 of a CMUT array 11, e.g. to operate the CMUT elements in collapse mode, as is well-known per se although it should be understood that embodiments of the present invention are not limited to CMUT-based ultrasound probes 10 and that any suitable ultrasound probe may be used in the ultrasound imaging system 1 of the present invention. The transducer controller 18 may be further adapted to control the voltage supply 45 such as to switch the ultrasound transducer cells 130 to a low-power mode, e.g. in response to a temperature sensor signal indicative of the ultrasound transducer cells 130 reaching a critical temperature.

The partially beam-formed signals produced by the microbeam former 12 may be forwarded to the main beam former 20 where partially beam-formed signals from individual patches of transducer elements are combined into a fully beam-formed signal. For example, the main beam former 20 may have 128 channels, each of which receives a partially beam-formed signal from a patch of dozens or hundreds of ultrasound transducer cells 111 and/or from the individual ultrasound transducer elements of such ultrasound transducer cells 111. In this way the signals received by thousands of transducer elements of an ultrasound transducer array 100 can contribute efficiently to a single beam-formed signal.

The beam-formed signals are coupled to a signal processor 22, which may form part of the processor arrangement 210 as previously explained. The signal processor 22 can process the received echo signals in various ways, such as bandpass filtering, decimation, I and Q component separation, and harmonic signal separation which acts to separate linear and nonlinear signals so as to enable the identification of nonlinear (higher harmonics of the fundamental frequency) echo signals returned from tissue and microbubbles. The signal processor 22 optionally may perform additional signal enhancement such as speckle reduction, signal compounding, and noise elimination. The bandpass filter in the signal processor 22 may be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals may be forwarded to a B-mode processor 26 and optionally to a Doppler processor 28, each of which may form part of the processor arrangement 210. The B-mode processor 26 employs detection of an amplitude of the received ultrasound signal for the imaging of structures in the body such as the tissue of organs and vessels in the body. B-mode images of structure of the body may be formed in either the harmonic image mode or the fundamental image mode or a combination of both for instance as described in U.S. Pat. No. 6,283,919 (Roundhill et al.) and U.S. Pat. No. 6,458,083 (Jago et al.)

The Doppler processor 28, if present, processes temporally distinct signals from tissue movement and blood flow for the detection of the motion of substances, such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material.

This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor may receive and process a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue. The structural and motion signals produced by the B-mode (and Doppler) processor(s) are coupled to a scan converter 32 and a multiplanar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image.

The scan converter can overlay a B-mode structural image with colors corresponding to motion at points in the image field with their Doppler-estimated velocities to produce a color Doppler image which depicts the motion of tissue and blood flow in the image field. The multiplanar reformatter 44 will convert echoes which are received from points in a common plane in a volumetric region of the body into an ultrasonic image of that plane, for instance as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multiplanar reformatter 44, and volume renderer 42 to an image processor 30 for further enhancement, buffering and temporary storage for display on an image display 50. The image processor 30 may form a part of the processor arrangement 210 and may further be adapted to control the visualization of volume slices as explained above. In addition to being used for imaging, the blood flow values produced by the Doppler processor 28 and tissue structure information produced by the B-mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made.

Output data from the quantification processor is coupled to a graphics processor 36 for the reproduction of measurement graphics and values with the image on the display 50. The graphics processor 36 can also generate graphic overlays for display with the ultrasound images. These graphic overlays can contain standard identifying information such as patient name, date and time of the image, imaging parameters, and the like. For these purposes the graphics processor receives input from the control panel 38, such as patient name.

The user interface 120 may be coupled to the transmit controller 18 to control the generation of ultrasound signals from the transducer array 11 and hence the images produced by the transducer array 11 and the ultrasound system 1. The user interface 120 also may be coupled to the multiplanar reformatter 44 for selection and control of the planes of multiple multiplanar reformatted (MPR) images which may be used to perform quantified measures in the image field of the MPR images. At least parts of the above described functionality of the ultrasound imaging system 100 may be implanted with the processor arrangement 210 as will be immediately apparent to the skilled person.

Figure 8:
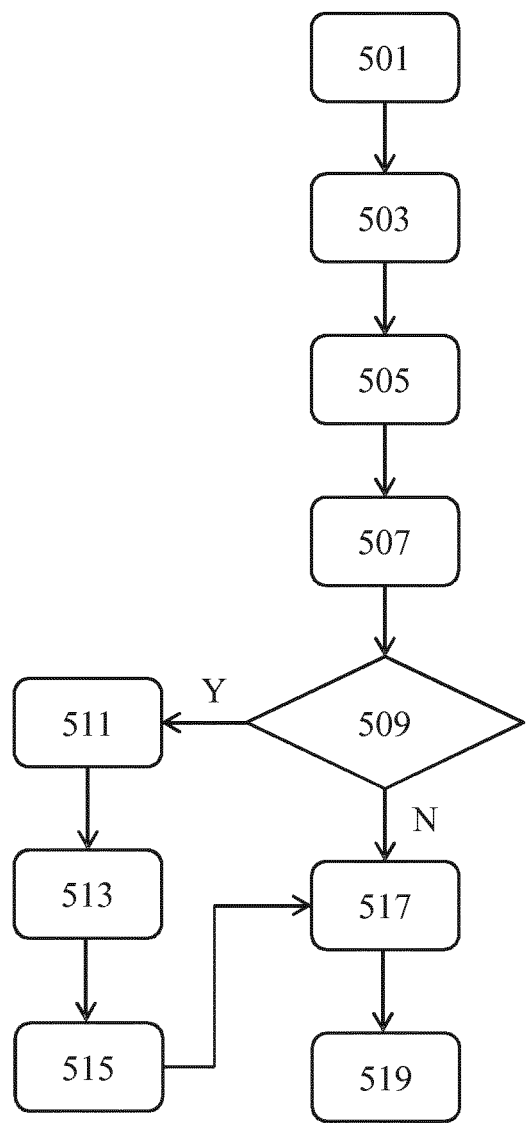
FIG. 8 is a flowchart of a method according to an example embodiment of the present invention.

In accordance with embodiments of the present invention, the processor arrangement 210 of the ultrasound image processing apparatus 200 is adapted to implement the method 500, a flow chart of which is depicted in FIG. 8. In other words, the method 500 is a computer-implemented method in the sense that the method is implemented on an apparatus comprising computational capability, such as the ultrasound image processing apparatus 200.

In accordance with embodiments of the present invention, an operator of the ultrasound image processing apparatus 200 may operate the apparatus in the so-called volume rendering mode, in which the apparatus renders a volumetric image for display on the display apparatus 50 from the 3-D ultrasound image or 2-D image slices captured with the ultrasound probe 10 of the ultrasound system 100, which image slices may have captured using an ultrasound probe 10 deploying mechanical or electronic steering as previously explained. The rendered volumetric image typically comprises an anatomical object of interest, such as a fetus 8, although it should be understood that the teachings of the present invention are not limited to fetal ultrasound but may be applied to the ultrasound imaging of any anatomical object of interest onto which a clinician may wish to perform a diagnostic evaluation such as a biometric measurement of a feature of interest of the anatomical object, such as for example an organ of interest of a patient 13 under investigation, such as the heart, the brain or the like of such a patient.

In an embodiment, the processor arrangement 210 receives a 3-D ultrasound image or a sequence of 2-D ultrasound images in operation 501 of the method 500, which data may be received in real time from the ultrasound probe 10 or alternatively may be retrieved from the data storage arrangement 220, e.g. in the case of off-line evaluation of the ultrasound image data captured with the ultrasound probe 10, such as upon completion of an examination of a patient 13. The processor arrangement 210 next processes this image data in operation 503 of the method 500 in order to render a volumetric ultrasound image. This may be preceded by generating a 3-D ultrasound image from the received sequence, in case of a sequence of 2-D ultrasound image frames having been generated with the probe 10. Any suitable type of volume rendering such as direct volume rendering, surface rendering, maximum or minimum intensity projection rendering and so on may be deployed. As such rendering techniques are well-known per se, they will not be explained in further detail for the sake of brevity only. The processor arrangement 210 controls the display apparatus 50 to display the rendered volumetric ultrasound image 300. Again, such control is entirely routine to the skilled person and will therefore not be explained in further detail for the sake of brevity only.

Figure 4:
FIG. 4 depicts an image of a rendered volumetric ultrasound image.

FIG. 4 depicts an image of such a volume rendered image 300, in which an anatomical object of interest, here a fetus 8, has been captured. The user may be interested in obtaining a view of a particular feature of the anatomical object of interest, e.g. a part of the anatomy of this object, in 2-D mode, for example to evaluate the anatomical feature of interest in an optimal view and/or to perform a biometric measurement of the anatomical feature of interest. To this end, the user may wish to generate a 2-D slice of the rendered volumetric ultrasound image 300 in which the anatomical feature of interest or at least a substantial part thereof, e.g. a cross-section thereof, lies in the plane of this generated 2-D slice. However, it is not straightforward for the user to obtain such a 2-D slice from such a rendered volumetric ultrasound image 300.

Figure 5:
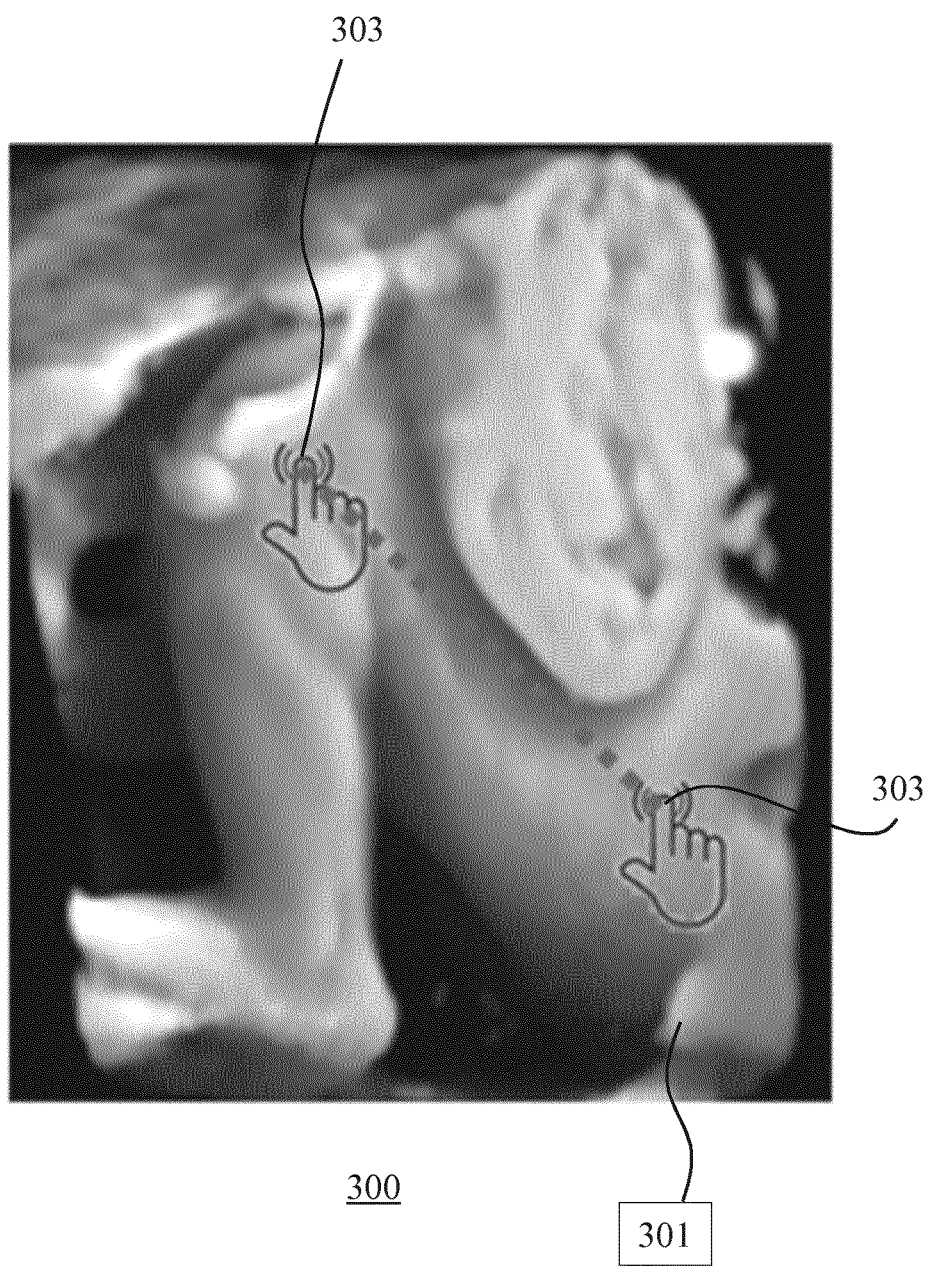
FIG. 5 schematically depicts an image of the rendered volumetric ultrasound image in which a user has identified points of interest in accordance with an example embodiment of the present invention.

In embodiments of the present invention, the user may specify a number of points 303 in the volumetric ultrasound image 300 to highlight the anatomical feature of interest, or at least a view expected to align with this feature, as schematically depicted in FIG. 5, with the dashed line connecting the user-specified points 303 indicating this anatomical feature or view. The user may specify the two or more points 303 in any suitable manner. Particularly preferred for ease of use and intuitive interaction with the display apparatus 50 is that the display apparatus 50 comprises a touchscreen onto which the volumetric ultrasound image 300 is displayed, such that the user can simply touch the touchscreen in order to specify the two or more points 303, for example by running a finger across a desired trajectory on the touchscreen or by tapping discrete points on the touchscreen. However, alternative ways of specifying the points 303 equally may be contemplated. For example, the user may move a cursor, crosshairs or other suitable location identifier across the screen of the display apparatus 50 using a controller such as a mouse, trackball or the like, in which case the user may specify the two or more points 303 by providing a point selection command with the location identifier in the location of the point to be selected, which point selection command may be provided in any suitable manner, e.g. through a button or the like on the controller or on a separate user interface such as a keyboard or the like. It should be understood that any suitable manner in which the user can select the points 303 may be deployed.

In operation 505 of the method 500, the processor arrangement 210 receives the user-selected points 303, e.g. through communication with the display apparatus 50 and/or with a user interface such as the user interface 120 used by the user to select the points 303, with the processor arrangement 210 processing the user-selected points 303 to link each of these points to a particular location within the volume rendered ultrasound image 300. In the volume rendered ultrasound image 300, each pixel of the image of the rendering result displayed on the display apparatus 50 is typically associated with depth information regarding the volume rendered image 300, e.g. a depth map. For example, the volume rendered image 300 may depict an iso-surface 301, which may have been derived from pixel intensity information in the 2-D image slices that have been processed to generate the volume rendered image 300, such that it will be known at which depth within the volume rendered image 300 a user's viewing angle or view ray of the image will coincide with the iso-surface 301. Alternatively, in scenarios where a transfer table is being used, integration of the image information along such a view path can be used to estimate the depth value mostly contributing to the pixel coinciding with that view path.

In operation 507 of the method 500, the processor arrangement 210 uses this depth information to define a 3-D path 307 in the volumetric ultrasound image 300, as schematically depicted in FIG. 6, in which non-limiting example the 3-D path 307 follows the outer contours of part of the leg of the fetus 8, which has been derived from a number of points 303 defined by the user of the ultrasound image processing apparatus 200 as previously explained, with the processor arrangement 210 of this apparatus mapping each of the user-specified points 303 onto a location at a determined depth within the volumetric ultrasound image 300 as explained above. The processor arrangement 210 may be adapted to deploy any suitable algorithms to identify the 3-D path 307, such as for example regression or outlier suppression algorithms to obtain meaningful 3-D curves in noisy volumetric images or in volumetric images containing artefacts.

In an embodiment, the processor arrangement 200 is adapted to control the display apparatus 50 such that the 3-D path 307 is displayed within the volume rendered ultrasound image 300, thereby giving the user visual feedback based on which user may decide if the 3-D path 307 has been appropriately defined by the processor arrangement 210, in which case the method may proceed to operation 509, or based on which the user may decide that refinement of the 3-D path 307 is required, at which point the user may interact with the display apparatus 50 to adjust the positioning of the 3-D path 307, e.g. by altering one or more of the previously defined points 303 or in any other suitable manner.

At this point, two main embodiments of the present invention will be explained in more detail. This is depicted in FIG. 8 by the operation 509 in which one of the two main embodiments is chosen. It should be understood however that operation 509 has been included for the sake of clarity only and that it is by no means necessary to decide with main embodiment to follow after operation 507. It is for example equally feasible to decide which main embodiment is followed before invoking the method 500 or at any suitable point in time during execution of the method 500.

In the first main embodiment, the user may wish to rely on the processor arrangement 210 to perform an automated biometric measurement of an anatomical feature of interest associated with the 3-D path 307. This is checked in operation 509, and if it is the case that the user wishes to rely on such an automated biometric measurement, the method 500 proceeds to operation 511 in which the processor arrangement 210 defines a volume of interest 309 associated with the 3-D path 307. Such a volume of interest 309 may be defined around the 3-D path 307. In some embodiments, the volume of interest 309 may not be centred around the 3-D path 307 but may be defined from the 3-D path 307 and extend from this path into a volume portion of the volumetric ultrasound image 300, which for instance may increase the likelihood of detecting an anatomical feature of interest 311 within the volume of interest 309 in case the 3-D path 307 delimits a (body) surface of the anatomical object of interest. The volume of interest 309 may have any suitable shape such as for example a tubular shape having a circular cross-section, which tubular shape follows the 3-D path 307 as previously explained. Other shapes of the volume of interest 309 may be equally contemplated as will be apparent to the skilled person.

Upon definition of the volume of interest 309, the volume of interest 309 may be investigated by the processor arrangement 210 in order to identify the anatomical feature of interest 311 within this volume in operation 513. This for example may be achieved using an appropriate image filter or segmentation algorithm adapted to identify such an anatomical feature of interest 311. Such image filters and segmentation algorithm are well-known to the skilled person and are therefore not explained in further detail for the sake of brevity only. In the remainder, where reference is made to an image filter, it should be understood that this is intended to also cover segmentation algorithms.

When it is clear what anatomical feature 311 the user is interested in, the appropriate image filter for detecting this anatomical feature 311 within the volume of interest 309 may be deployed. For example, where the user has identified the anatomical feature of interest 311, such as a fetal femur length, the image filter for fetal femur detection may be deployed by the processor arrangement 210. Alternatively, where it is prima facie unknown what anatomical feature 311 the user is interested in, the processor arrangement 210 may deploy a plurality of image filters to detect different anatomical features 311 and select the filtering result in which an anatomical feature 311 was identified with the highest degree of confidence, which is indicative of a best match between the applied image filter and the anatomical feature 311.

If no anatomical feature 311 can be identified in the volume of interest 309, the volume of interest 309 may be rescaled, e.g. its cross-sectional size increased, after which operation 513 is repeated. If after a defined number of such iterations the anatomical feature 311 still cannot be identified, the user may be presented with a warning signal or message, e.g. a message is displayed on the display apparatus 50. Once the anatomical feature of interest 311 has been identified, the processor arrangement 210 may perform a biometric measurement on the identified anatomical feature of interest 311 in operation 515 in any suitable manner. Such automated biometric measurements are well-known per se and are therefore not explained in further detail for the sake of brevity only. This may be any suitable biometric measurement such as a length, thickness or cross-section measurement of the anatomical feature of interest 311.

Figure 7:
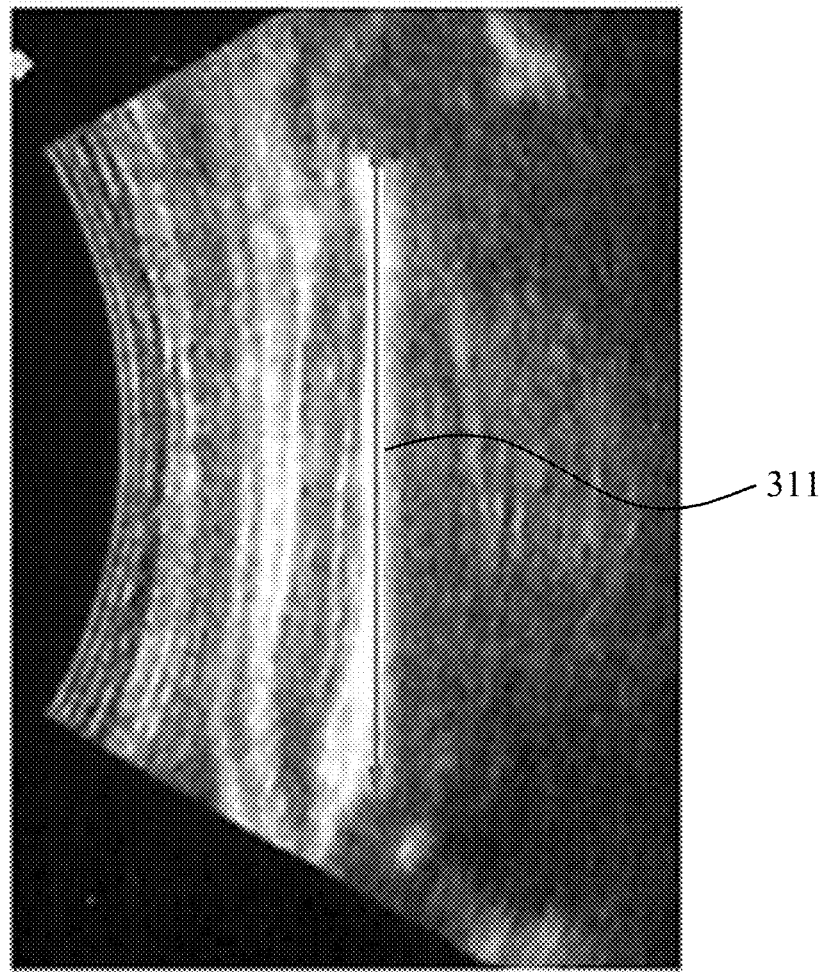
FIG. 7 schematically depicts a 2-D image slice extracted from the rendered volumetric ultrasound image based on the user-identified points of interest in accordance with an example embodiment of the present invention.

Following the completion of the biometric measurement, or alternatively following the second main embodiment in which the user has indicated that a manual biometric measurement of an anatomical feature of interest is to be performed such that the aforementioned operations 511, 513 and 515 are omitted, the method 500 proceeds to operation 517 in which the processor arrangement 210 generates a 2-D image slice 400 based on the constructed 3-D path 307 as schematically depicted in FIG. 7, with the processor arrangement 210 adapted to control the display apparatus 50 to display the generated 2-D image slice 400 in operation 519. The 2-D image slice 400 preferably is arranged tangentially to the 3-D path 307 such that an anatomical feature of interest 311 (if present) lies in the plane of the 2-D image slice 400. In other words, the processor arrangement 210 generates an optimal viewing plane of such an anatomical feature of interest 311 based on which the user may perform manual biometric measurements of the anatomical feature of interest 311 as indicated by the double arrow in FIG. 7 with a minimal risk of such measurements being inaccurate, e.g. due to foreshortening of the anatomical feature of interest 311 by viewing this feature under a non-optimal angle in which the feature appears shorter as explained in more detail above.

Where such biometric measurements have been performed in accordance with the first main embodiment of the present invention, the processor arrangement 210 may be further adapted to display the biometric measurement results on the display apparatus 50 in operation 519. The processor arrangement 210 preferably displays the biometric measurement results together with the generated 2-D image slice 400, e.g. as an overlay of this image slice, adjacent to this image slice, and so on, although in an alternative embodiment of the first main embodiment of the present invention the processor arrangement 210 may simply display the biometric measurement results on their own, i.e. without displaying the 2-D image slice 400, in which case operation 517 may be skipped.

The 2-D image slice 400 may be generated by the processor arrangement 210 in any suitable manner. In a particularly advantageous embodiment, a best fitting tangential plane to the 3-D path 307 is estimated, for example by fitting a plurality of tangential planes to the 3-D path 307 and selecting the plane having the best fit with this path. The view geometry may be changed in accordance with the selected tangential plane such that the view direction is now parallel to the normal of this plane. This may be refined by selecting the plane having the best fit with this path within a range of view orientations around the current view orientation of the rendered volumetric image such as to limit the change in view orientation relative to the rendered volumetric image, as large changes in such view orientation may be experienced as confusing by the user.

At this point, it is noted that the 3-D path 307 derived from the depth information associated with the pixels of the volumetric image corresponding to the user-specified points 303 is not necessarily leveraged to generate a 2-D image slice 400. In alternative embodiments of the method 300 (not explicitly shown), the processor arrangement 210 may use the 3-D path in further processing operations.

A first example processing operation is the determination of the length of the 3-D path 307, which may provide an accurate biometric measurement of an anatomical feature of interest in an automated fashion, which for example is useful where a user has sufficient confidence in such an automated biometric measurement. In such a scenario, the generation of the 2-D image slice 400 may not be required in order to obtain the desired biometric measurement.

A second example processing operation is the reorientation of the rendered volumetric image (rather than the generation of 2-D image slice 400) based on the 3-D path 307, in which a main direction of the path (i.e. an anatomical feature of interest associated with the path) is oriented perpendicular to the viewing angle of the rendered volumetric image such that the anatomical feature of interest extends across the screen of the display apparatus 50, which facilitates the evaluation of the anatomical feature of interest by the user of the apparatus. Other reorientations, e.g. a reorientation in which the main direction of the path 307 is oriented parallel to the viewing angle of the rendered volumetric image may of course also be contemplated.

The above described embodiments of the method 300 may be realized by computer readable program instructions embodied on a computer readable storage medium having, when executed on a processor arrangement 200, cause the processor arrangement to implement the method 300. Any suitable computer readable storage medium may be used for this purpose, such as for example an optically readable medium such as a CD, DVD or Blu-Ray disc, a magnetically readable medium such as a hard disk, an electronic data storage device such as a memory stick or the like, and so on. The computer readable storage medium may be a medium that is accessible over a network such as the Internet, such that the computer readable program instructions may be accessed over the network. For example, the computer readable storage medium may be a network-attached storage device, a storage area network, cloud storage or the like. The computer readable storage medium may be an Internet-accessible service from which the computer readable program instructions may be obtained. In an embodiment, the ultrasound image processing apparatus 200 is adapted to retrieve the computer readable program instructions from such a computer readable storage medium and to create a new computer readable storage medium by storing the retrieved computer readable program instructions in the data storage arrangement 220, e.g. in a memory device or the like forming part of the data storage arrangement 220.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. The word "comprising" does not exclude the presence of elements or steps other than those listed in a claim. The word "a" or "an" preceding an element does not exclude the presence of a plurality of such elements. The invention can be implemented by means of hardware comprising several distinct elements. In the device claim enumerating several means, several of these means can be embodied by one and the same item of hardware. The mere fact that certain measures are recited in mutually different dependent claims does not indicate that a combination of these measures cannot be used to advantage.

The invention claimed is:

1. An ultrasound image processing apparatus for obtaining biometric measurements of an anatomical feature of interest from a 3-D ultrasound image, the ultrasound image processing apparatus comprising:
   a display;
   a processor communicatively coupled to the display; and
   a non-transitory memory storing instructions that, when executed by the processor, cause the processor to:
   render a volumetric ultrasound image from the 3-D ultrasound image and control the display apparatus to display the rendered volumetric ultrasound image;
   receive a plurality of user inputs highlighting the anatomical feature of interest, wherein each user input defines a point with a corresponding pixel of the displayed volumetric ultrasound image;
   estimate a depth represented by each of the corresponding pixels in the volumetric ultrasound image, wherein the estimated depth of each corresponding pixel comprises a depth in the volumetric ultrasound image having a highest contribution to pixel intensity of the corresponding pixel;

define a 3-D path in the volumetric ultrasound image based on the received user inputs along the estimated depths, wherein the defined 3-D path comprises the corresponding pixels;

measure a length of the defined 3-D path in the volumetric ultrasound image; and control the display apparatus to display the measured length of the defined 3-D path.

2. The ultrasound image processing apparatus of claim 1, wherein the instructions further cause the processor to generate the 3-D ultrasound image from a sequence of 2-D ultrasound images.

3. The ultrasound image processing apparatus of claim 1, wherein the instructions further cause the processor to:
generate a 2-D image slice of the 3-D ultrasound image based on the defined 3-D path, wherein at least a part of the anatomical feature of interest lies in a plane of the 2-D image slice.

4. The ultrasound image processing apparatus of claim 3, wherein the instructions further cause the processor to generate the 2-D image slice based on the defined 3-D path by:
fitting a plurality of tangential planes to different regions of the defined 3-D path;
selecting the tangential plane having a best fit with the defined 3-D path; and
generating the 2-D image slice in accordance with the selected tangential plane.

5. The ultrasound image processing apparatus of claim 3, wherein the instructions further cause the processor to:
perform a biometric measurement on the anatomical feature of interest visible within the generated 2-D image slice, wherein the biometric measurement comprises at least one of length, thickness or cross-section measurement of the anatomical feature of interest; and
control the display apparatus to display a result of the performed biometric measurement.

6. The ultrasound image processing apparatus of claim 5, wherein the instructions further cause the processor to control the display to display the result of the performed biometric measurement by controlling the display to display the generated 2-D image slice together with the result of the performed biometric measurement.

7. The ultrasound image processing apparatus of claim 5, wherein the instructions further cause the processor to perform the biometric measurement on the anatomical feature of interest visible within the generated 2-D image slice by:
defining a volume of interest associated with the defined 3-D path; and
identifying the anatomical feature of interest within the volume of interest.

8. The ultrasound image processing apparatus of claim 7, wherein the instructions further cause the processor to identify the anatomical feature of interest within the volume of interest by:
applying a plurality of image filters to the volume of interest; and
identifying the anatomical feature of interest based on the filter results obtained by the plurality of image filters.

9. The ultrasound image processing apparatus of claim 3, wherein the length of the 3-D path is measured in the 2-D image slice of the 3-D ultrasound image.

10. The ultrasound image processing apparatus of claim 3, wherein the instructions further cause the processor to:
reorient the rendered volumetric ultrasound image based on the defined 3-D path, wherein a main direction of the 3-D path is oriented perpendicular to a viewing angle of the rendered volumetric image.

11. An ultrasound imaging system comprising the ultrasound image processing apparatus of claim 1 and an ultrasound probe for providing the ultrasound image processing apparatus with ultrasound image data for forming the 3-D ultrasound image.

12. A computer-implemented method for obtaining biometric measurements of an anatomical feature of interest from a 3-D ultrasound image, the method comprising:
receiving the 3-D ultrasound image;
rendering a volumetric ultrasound image from the 3-D ultrasound image and controlling a display apparatus to display the rendered volumetric ultrasound image;
receiving a plurality of user inputs highlighting the anatomical feature of interest, wherein each user input defines a point with a corresponding pixel of the displayed volumetric ultrasound image;
estimating a depth represented by each of the corresponding pixels in the volumetric ultrasound image, wherein the estimated depth of each corresponding pixel comprises a depth in the volumetric ultrasound image having a highest contribution to pixel intensity of the corresponding pixel;
defining a 3-D path in the volumetric ultrasound image based on the received user inputs along the estimated depths, wherein the defined 3-D path comprises the corresponding pixels;
measuring a length of the defined 3-D path in the volumetric ultrasound image; and
controlling the display apparatus to display the measured length of the defined 3-D path.

13. The computer-implemented method of claim 12, further comprising receiving a sequence of 2-D ultrasound images, and generating the 3-D ultrasound image from the sequence of 2-D ultrasound images.

14. The computer-implemented method of claim 12, further comprising:
generating a 2-D image slice of the 3-D ultrasound image based on the defined 3-D path, wherein at least a part of the anatomical feature of interest lies in a plane of the 2-D image slice.

15. The computer-implemented method of claim 14, wherein generating the 2-D image slice based on the defined 3-D path comprises:
fitting a plurality of tangential planes to different regions of the defined 3-D path;
selecting the tangential plane having a best fit with the defined 3-D path; and
generating the 2-D image slice in accordance with the selected tangential plane.

16. The computer-implemented method of claim 6, further comprising:
performing a biometric measurement on the anatomical feature of interest visible within the generated 2-D image slice, wherein the biometric measurement comprises at least one of length, thickness or cross-section measurement of the anatomical feature of interest; and
controlling the display apparatus to display a result of the performed biometric measurement with the generated 2-D image slice.

17. The computer-implemented method of claim 16, wherein performing the biometric measurement on the anatomical feature of interest visible within the generated 2-D image slice comprises:
- defining a volume of interest associated with the defined 3-D path; and
- identifying the anatomical feature of interest within the volume of interest.

18. The computer-implemented method of claim 17, wherein identifying the anatomical feature of interest within the volume of interest comprises:
- applying a plurality of image filters to the volume of interest; and
- identifying the anatomical feature of interest based on filter results obtained by the plurality of image filters.

19. The computer-implemented method of claim 14, wherein the length of the 3-D path is measured in the 2-D image slice of the 3-D ultrasound image.

20. The computer-implemented method of claim 12, further comprising:
- reorienting the rendered volumetric ultrasound image based on the defined 3-D path, wherein a main direction of the 3-D path is oriented perpendicular to a viewing angle of the rendered volumetric image.

* * * * *